US00PP17512P3

(12) United States Plant Patent
Larsen

(10) Patent No.: US PP17,512 P3
(45) Date of Patent: Mar. 20, 2007

(54) ***OSTEOSPERMUM* PLANT NAMED 'SUNNY ANTIQUE SERENA'**

(50) Latin Name: *Osteospermum ecklonis*
Varietal Denomination: Sunny Antique Serena

(75) Inventor: Bjarne Nyholm Larsen, Odense (DK)

(73) Assignee: Sunny Gronnegyden APS, Odense (DK)

( * ) Notice: Subject to any disclaimer, the term of this patent is extended or adjusted under 35 U.S.C. 154(b) by 17 days.

(21) Appl. No.: 11/094,123

(22) Filed: Mar. 31, 2005

(65) Prior Publication Data

US 2006/0225178 P1 Oct. 5, 2006

(51) Int. Cl.
*A01H 5/00* (2006.01)

(52) U.S. Cl. ..... Plt./360
(58) Field of Classification Search ..... Plt./360
See application file for complete search history.

(56) References Cited

PUBLICATIONS

Extract from the Register of the Community Variety Rights dated Jan. 31, 2005 (1 pg.), together with the Certificate on the Grant of Community Plant Variety Rights for 'Sunny Antique Serena' (1 pg.).

*Primary Examiner*—Kent Bell
(74) *Attorney, Agent, or Firm*—Foley & Lardner LLP

(57) ABSTRACT

A new and distinct cultivar of *Osteospermum* plant named 'Sunny Antique Serena' characterized by its unique color combinations on the upper and undersides of its ray florets: (upperside) when opening—RHS 5C to RHS 5D, yellow and when fully opened—RHS 11D, yellow; (underside) when opening and when fully opened—longitudinal stripes of alternating gray-orange colors, RHS N163A and RHS N163B, gray-orange; upright, compact and globular plant habit; dense and bushy growth habit, mainly due to upright stems; moderately vigorous growth habit, but less need for chemical growth retardation; and high number of inflorescences per plant.

2 Drawing Sheets

Figure 1:
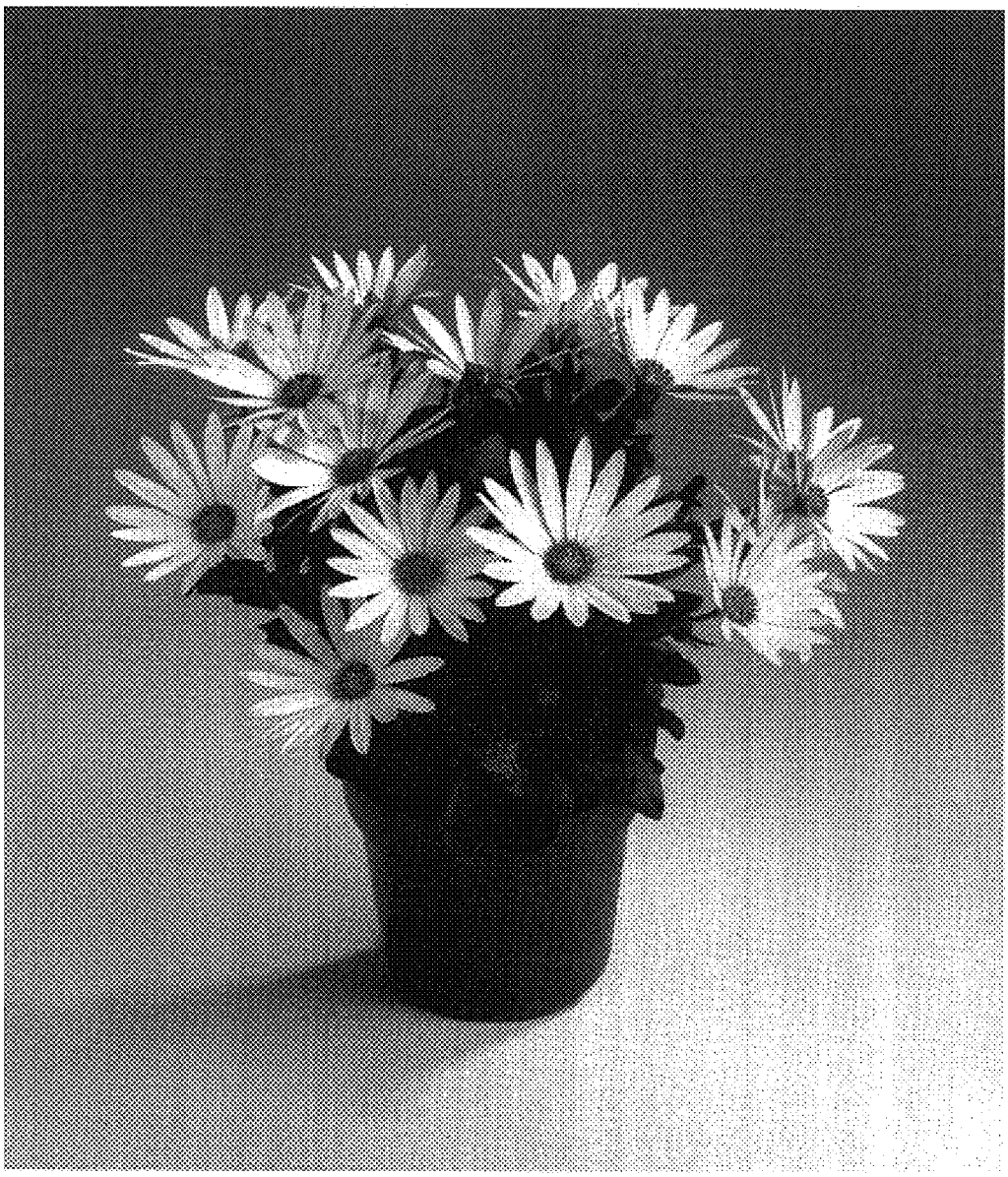

Botanical designation: *Osteospermum ecklonis.*
Variety denomination: 'Sunny Antique Serena'.

BACKGROUND OF THE INVENTION

The present Invention relates to a new and distinct cultivar of *Osteospermum* plant, botanically known as *Osteospermum ecklonis* (*DC*) *T. Norl.,* commonly known as Cape Daisy and hereinafter referred to by the variety denomination 'Sunny Antique Serena'.

The new *Osteospermum* cultivar is a product of a planned breeding program conducted by the Inventor, Bjarne Nyholm Larsen, in Stige, Denmark. The objective of the breeding program is to create new compact *Osteospermums* with continuous flowering, good postproduction longevity and attractive inflorescence coloration.

The new *Osteospermum* cultivar originated as a naturally occurring whole plant mutation found as a single plant in a production batch of *Osteospermum ecklonis* (*DC*) *T. Norl.* designated 'Sunny Serena' (patented, and disclosed in U.S. Plant Pat. No. 15,693 and CPVO Registration Number 10371) in March of 2002 in Stige, Denmark. The new *Osteospermum* cultivar originated from a naturally occurring mutation found in a production batch of *Osteospermum ecklonis* (*DC*) *T. Norl.* designated 'Sunny Serena' in March of 2002 in Stige, Denmark. The Inventor selected the new *Osteospermum* cultivar in June of 2002 on the basis of its attractive inflorescence color, good postproduction longevity, continuous flowering and upright, compact, freely branching growth habit.

Asexual reproduction of the new *Osteospermum* cultivar by terminal cuttings taken and propagated at trial production batches in Stige, Denmark, since 2003 has demonstrated that the combination of characteristics as herein disclosed for the new cultivar are firmly fixed and retained through successive generations of asexual reproduction. The new *Osteospermum* cultivar reproduces true-to-type.

SUMMARY OF THE INVENTION

The following traits have been repeatedly observed and are determined to be the unique characteristics of 'Sunny Antique Serena'. These characteristics in combination distinguish 'Sunny Antique Serena' as a new and distinct cultivar:

1. Unique color combination of upper and underside of ray florets: (upperside) when opening—RHS 5C to RHS 5D, yellow and when fully opened—RHS 11D, yellow; (underside) when opening and when fully opened—longitudinal stripes of alternating gray-orange colors, RHS N163A and RHS N163B, gray-orange;
2. Upright, compact and globular plant habit;
3. Dense and bushy growth habit, mainly due to upright stems;
4. Moderately vigorous growth habit, but less need for chemical growth retardation; and
5. High number of inflorescences per plant.

Plants of the *Osteospermum* cultivar 'Sunny Antique Serena' and plants of the cultivar 'Sunny Serena' differ in inflorescence color. Plants of 'Sunny Antique Serena' have a color combination of yellow to gray-orange ray florets with dark gray-green disc florets, whereas plants of 'Sunny Serena' have a color combination of gray-orange, gray-yellow, yellow-white and yellow ray florets with silvery gray and gray white disc florets.

Of the many commercial cultivars known to the Inventor, the most similar in comparison to the *Osteospermum* cultivar 'Sunny Antique Serena' is the cultivar 'Sunny Serena' (patented, and disclosed in U.S. Plant Pat. No. 15,693 and CPVO Registration Number 10371).

BRIEF DESCRIPTION OF THE PHOTOGRAPHS

The accompanying colored photographs illustrate the overall appearance of the new *Osteospermum* cultivar 'Sunny Antique Serena' showing the colors as true as is reasonably possible with colored reproductions of this type. Colors in the photographs may differ slightly from the color values cited in the detailed botanical description which accurately describe the color of the new *Osteospermum* cultivar 'Sunny Antique Serena'.

The first photograph (FIG. 1) shows a side perspective view of a typical flowering plant of 'Sunny Antique Serena' as grown in an 11 cm pot.

Figure 2:
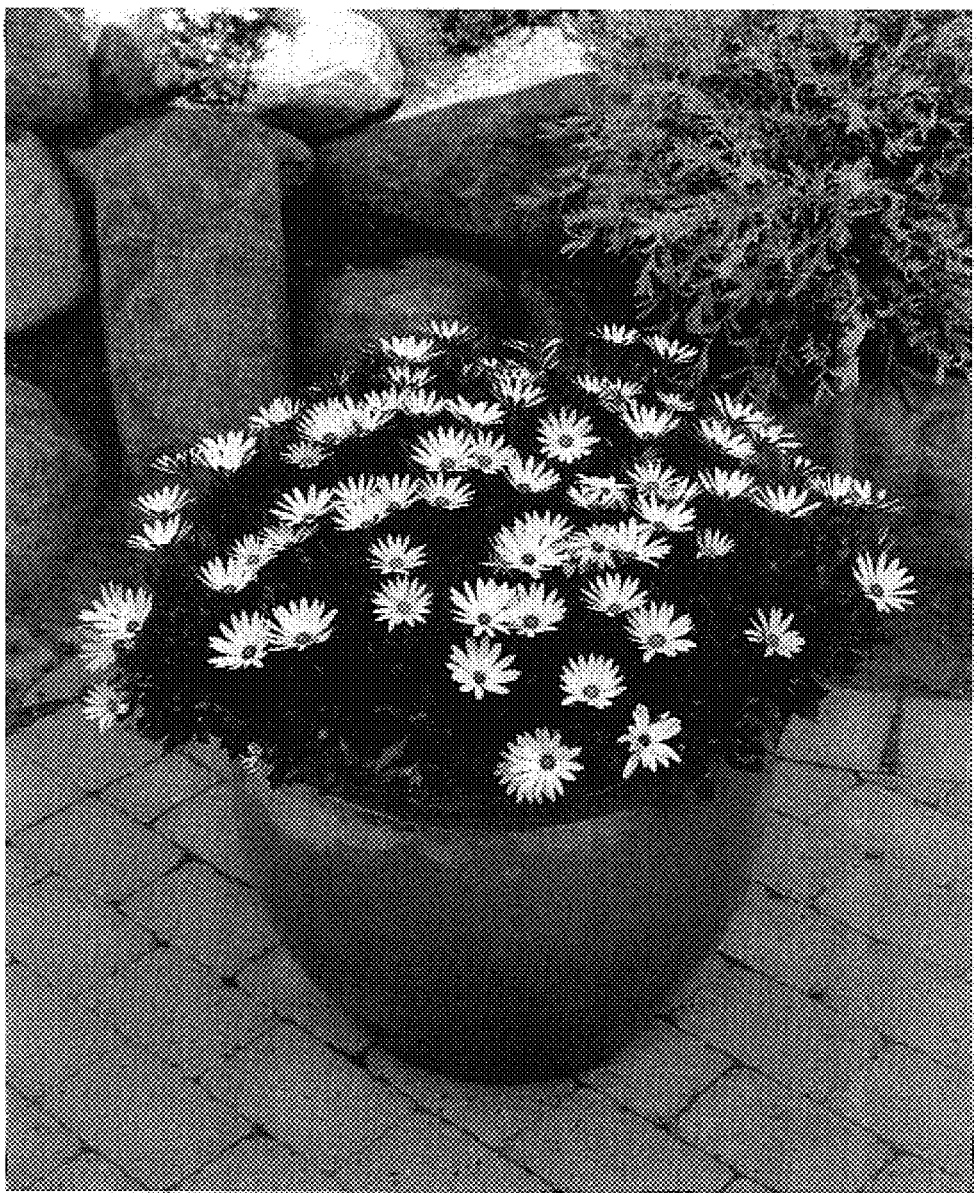

The second photograph (FIG. 2) shows a side perspective view of numerous plants of 'Sunny Antique Serena' as grown in a large display pot.

DETAILED BOTANICAL DESCRIPTION

Plants of the new *Osteospermum* cultivar 'Sunny Antique Serena' have not been observed under all possible environmental conditions. The phenotype may vary somewhat with variations in environment such as temperature, light intensity, daylength, and fertility level without any variance in the genotype of the plant.

The aforementioned photographs, together with the following observations, measurements and values describe plants of the new *Osteospermum* cultivar 'Sunny Antique Serena' as grown in a heated and lighted, glass-covered greenhouse in Fyn, Denmark, under conditions which closely approximate those generally used in commercial practice. Plants of the new *Osteospermum* cultivar 'Sunny Antique Serena' were grown in natural long days with 15 to 20 hours of daylight. Chlormequat treatments 3×0.5% drench were also used when growing 'Sunny Antique Serena'.

The age of the 'Sunny Antique Serena' plants described is 20 weeks old after cutting and grown in 11 cm pots. The photographs and descriptions were taken during the spring season when outdoor day temperatures range from 16 to 22° C. and when outdoor night average temperature range from 16 to 18° C.

Color references are made to The Royal Horticultural Society Colour Chart (R.H.S.), 4$^{th}$ ed., except where general colors of ordinary significance are used.

Botanical classification: *Osteospermum ecklonis*.

Parentage: *Osteospermum ecklonis* (*DC*) *T. Norl.* designated 'Sunny Serena' (patented, and disclosed in U.S. Plant Pat. No. 15,693 and CPVO Registration Number 10371).

Propagation:

*Type of cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Non-hardy perennial, potted or garden bedding plant. Globular, upright, with basal branching plant habit. *Osteospermum* inflorescences in composite heads. Freely branching with lateral flowering branches forming at every node; dense and bushy.

*Crop time.*—After rooting, about 20 weeks are required to produce finished flowering plants in 11 cm pots.

*Plant height* (*soil level to top of plant plane*).—About 20 cm.

*Plant spread* (*width*).—About 17 cm.

*Lateral branches.*—Quantity per plant: 4 primary and 7 secondary (flowering). Length (primary): 3 cm. Length (secondary): 7 to 12 cm. Diameter (primary and secondary): 4 to 5 mm. Quantity of leaves: 10 to 15 per lateral branch.

*Internode.*—Length: 3 mm.

*Stem.*—Shape: Round. Strength: Strong. Aspect: (main stem) upright, branches at 70 to 80° angle. Texture: Smooth, glabrous. Color: RHS 144C, yellow-green.

*Vigor.*—Moderately vigorous growth rate.

*Foliage description.*—Alternate (⅕ whorl), single, pinnate venation. Length: 2 to 4 cm. Width: 1 to 3 cm. Shape: Obovate to spatulate, 4 to 6 acuminate teeth. Apex: Obtuse. Base: Attenuate, decurrent. Margin: Broadly dentate (2 to 3 lobes on each side). Texture (both sides and edges): Pubescent with scattered short, stiff hairs. Color: Young foliage, upperside RHS 147A, yellow-green; underside RHS 148C, yellow-green. Mature foliage, upperside RHS 139B, green; underside RHS 147A, yellow-green.

*Venation.*—Color: upperside RHS 147C, yellow-green; underside not visible against background tissue. Pattern: Pinnate.

*Petiole.*—Length: 10 to 20 mm. Diameter: 2 to 4 mm. Shape: Flat, winged. Texture: Glabrous. Color: RHS 145B, yellow-green.

Inflorescence description:

*Inflorescence number per plant.*—About 20.

*Inflorescence arrangement and shape.*—Tubular disc florets and flat, lanceolate ray florets in composite daisy heads in leaf axils; with 15 parted involucre. Inflorescences face upright to 80° angle from vertical.

*Natural flowering season.*—Continuous throughout the spring and summer. Season can be extended by vernalization and long day treatments.

*Rate of inflorescence opening.*—About 3 per week.

*Inflorescence longevity on the plant.*—5 to 10 days; however, longevity of individual inflorescence is highly dependent on temperature and light conditions. Inflorescence persistent.

*Fragrance.*—Weak, fresh lemon fragrance.

*Number of inflorescence heads per lateral stem.*—2.

*Inflorescence size.*—Height; 6 mm capitulum. Diameter: 6 to 7 cm capitulum; 1 mm single disc floret.

Buds:

*Quantity per lateral stem.*—5. Length: Up to 12 mm. Diameter: Up to 10 mm. Rate of opening: 2 per plant per week. Shape: Globular. Color: From RHS 145C (base) to RHS N154B, yellow green.

Inflorescences:

Ray florets:

*Typical number of ray florets per inflorescence.*—About 20. Observed number of ray florets per inflorescence: 17 to 22. Arrangement: Sympetalous. Appearance: 3 or more furrows. Texture: Smooth, matte. Length: About 27 mm. Width (diameter): About 8 mm. Shape: Elliptic. Apex: Rounded with slight emargination. Base: Fused. Margin: Entire. Ray floret color: (upperside) when opening — RHS 5C to RHS 5D, yellow and when fully opened — RHS 11D, yellow; (underside) when opening and when fully opened — longitudinal stripes of alternating gray-orange colors, RHS N163A and RHS N163B, gray-orange.

Disc florets:

*Typical number of discs florets per inflorescence.*—About 65. Observed number of discs florets per inflorescence: 50 to 75. Arrangement: Sympetalous. Appearance: Translucent. Texture: Smooth, matte. Length: About 11 mm. Width (diameter): About 3 mm. Shape: Free tips attenuate. Base: Fused. Margin: Free tips entire. Disc floret color: (when opening and fully opened) upperside and underside RHS 176B, dark gray-green.

*Phyllary.*—Appearance: Involucre, 15 lanceolate units. Quantity of phyllaries: 15. Length: 6 to 12 mm. Width: 1 to 3 mm. Overall shape: Lanceolate. Apex: Acuminate. Base: Fused. Margin: Entire. Color: RHS 137D, green (no difference in RHS color designation depending on immature v. mature and upperside v. underside).

*Peduncle.*—Length: About 5 cm. Diameter: About 3 mm. Strength: Strong, stiff. Angle: 0 to 80° from vertical. Color: RHS 144C, yellow-green.

Reproductive organs:

*Androecium.*—Location: Disc florets only. Stamen: Quantity: 5, fused. Anthers: Shape: Linear, fused. Length: About 2 mm. Color: RHS N99B, blue. Pollen: Amount: Good production, plenty. Color: RHS N25A, orange.

*Gynoecium.*—Location: Ray and disc florets. Pistil: Quantity: 1. Length: About 4 mm. Stigma: Shape: Brush-like, cleft. Color: RHS N187A, purple. Style: Length: 2 mm. Color: Inconspicuous. Ovary: Color: RHS 2D, green-yellow.

*Seeds.*—Quantity: many, 10 to 20 per inflorescence. Length: About 2 to 3 mm. Diameter: About 1 mm. Texture: Smooth and glabrous. Color: gray-brown.

*Fruit.*—None.

*Growth retardants.*—Chlormequat 3×0.5% drench.

Weather tolerance: Plants of the new *Osteospermum* have exhibited good tolerance to drought, rain and wind, with low temperature resistance to 1° C.

Disease/pest resistance: Good.

Disease/pest susceptibility: Low.

I claim:

1. A new and distinct cultivar of *Osteospermum* plant named 'Sunny Antique Serena', as illustrated and described herein.

* * * * *